United States Patent
Van Dijk et al.

(10) Patent No.: US 10,441,313 B2
(45) Date of Patent: Oct. 15, 2019

(54) SPATIAL DIMENSION DETERMINATION DEVICE FOR DETERMINING A SPATIAL DIMENSION OF A TARGET ELEMENT WITHIN AN OBJECT

(71) Applicant: KONINKLIJKE PHILIPS N.V., Eindhoven (NL)

(72) Inventors: Erik Martinus Hubertus Petrus Van Dijk, Den Bosch (NL); Sander Slegt, Best (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 293 days.

(21) Appl. No.: 14/646,805

(22) PCT Filed: Dec. 4, 2013

(86) PCT No.: PCT/IB2013/060627
§ 371 (c)(1),
(2) Date: May 22, 2015

(87) PCT Pub. No.: WO2014/091366
PCT Pub. Date: Jun. 19, 2014

(65) Prior Publication Data
US 2015/0297312 A1 Oct. 22, 2015

Related U.S. Application Data

(60) Provisional application No. 61/735,695, filed on Dec. 11, 2012.

(51) Int. Cl.
*A61B 19/00* (2006.01)
*A61B 17/34* (2006.01)
(Continued)

(52) U.S. Cl.
CPC ............ *A61B 17/3403* (2013.01); *A61B 6/12* (2013.01); *A61B 6/547* (2013.01); *A61B 6/582* (2013.01);
(Continued)

(58) Field of Classification Search
None
See application file for complete search history.

(56) References Cited

U.S. PATENT DOCUMENTS 4,671,291 A * 6/1987 Wilson .............. A61M 25/0108
600/435
5,803,912 A * 9/1998 Siczek ................. A61B 6/0435
348/E13.014
(Continued)

FOREIGN PATENT DOCUMENTS

WO 2013169814 A1 11/2013
WO 2013175472 A2 11/2013
(Continued)

OTHER PUBLICATIONS

Riga, C.V. et al. "The role of robotic endovascular catheters in fenestrated stent grafting", Society for Vascular Surgery, vol. 51, No. 4, pp. 810-820, Apr. 2010, London, UK.
(Continued)

*Primary Examiner* — Thomas J Hong
*Assistant Examiner* — Helene Bor

(57) ABSTRACT

The invention relates to a spatial dimension determination device for determining a spatial dimension of a target element like a vessel within an object (9), for instance, within a person. Movement parameters describing a movement of an introduction element (4) moved by a moving unit (2) like a robot and several images showing the introduction element are used for determining a dimensional relation between an image dimension and a real dimension. A further (Continued)

image showing the target element is provided, wherein a real dimension of the target element is determined based on an image dimension of the target element in the further image and based on the determined dimensional relation. An unknown real physical dimension of a target element within the object can therefore accurately be determined from an image of the target element by using, inter alia, the movement parameters.

7 Claims, 2 Drawing Sheets

(51) Int. Cl.
| | | |
|---|---|---|
| *A61M 25/01* | (2006.01) | |
| *G01B 15/00* | (2006.01) | |
| *A61B 6/12* | (2006.01) | |
| *A61B 6/00* | (2006.01) | |
| *A61B 34/20* | (2016.01) | |
| *A61B 34/30* | (2016.01) | |
| *A61F 2/82* | (2013.01) | |
| *A61B 90/00* | (2016.01) | |

(52) U.S. Cl.
CPC .............. *A61B 34/20* (2016.02); *A61B 34/30* (2016.02); *A61M 25/0105* (2013.01); *G01B 15/00* (2013.01); *A61B 6/504* (2013.01); *A61B 2034/2065* (2016.02); *A61B 2034/301* (2016.02); *A61B 2090/364* (2016.02); *A61B 2090/376* (2016.02); *A61B 2090/3764* (2016.02); *A61F 2/82* (2013.01); *A61M 2025/0166* (2013.01)

(56) References Cited

U.S. PATENT DOCUMENTS

| | | | |
|---|---|---|---|
| 7,536,053 B2* | 5/2009 | Davidson-Sokal | G06T 5/006 382/100 |
| 7,603,159 B2* | 10/2009 | Rasche | A61B 6/12 600/424 |
| 2003/0120283 A1* | 6/2003 | Stoianovici | A61B 34/70 606/130 |
| 2005/0203371 A1* | 9/2005 | Kleen | A61M 25/0105 600/407 |
| 2007/0177166 A1 | 8/2007 | Habets | |
| 2009/0234444 A1 | 9/2009 | Maschke et al. | |
| 2011/0040150 A1 | 2/2011 | Altman et al. | |
| 2011/0306867 A1* | 12/2011 | Gopinathan | A61B 5/02007 600/407 |
| 2012/0071751 A1 | 3/2012 | Sra | |
| 2012/0071782 A1 | 3/2012 | Patil | |

FOREIGN PATENT DOCUMENTS

| | | |
|---|---|---|
| WO | 2014091347 A2 | 6/2014 |
| WO | 2014091380 A1 | 6/2014 |
| WO | 2014162275 A1 | 10/2014 |

OTHER PUBLICATIONS

Corral, G. et al., "Robot control by fluoroscopic guidance for minimally invasive spine procedures", Computer Assisted Radiology and Surgery, Proceedings of the 18th International Congress, Science Direct, vol. 1268, Jun. 2004, pp. 509-514.

* cited by examiner

SPATIAL DIMENSION DETERMINATION DEVICE FOR DETERMINING A SPATIAL DIMENSION OF A TARGET ELEMENT WITHIN AN OBJECT

CROSS-REFERENCE TO PRIOR APPLICATIONS

This application is the U.S. National Phase application under 35 U.S.C. § 371 of International Application Serial No. PCT/IB2013/060627, filed on Dec. 4, 2013, which claims the benefit of U.S. Application Ser. No. 61/735,695, filed on Dec. 11, 2012. These applications are hereby incorporated by reference herein.

FIELD OF THE INVENTION

The invention relates to a spatial dimension determination device, a spatial dimension determination method and a spatial dimension determination computer program for determining a spatial dimension of a target element within an object. The invention relates further to an interventional system, an interventional method and an interventional computer program comprising an introduction element like a catheter for being introduced into an object.

BACKGROUND OF THE INVENTION

A C-arm x-ray imaging system comprises an x-ray source and an x-ray detector for generating x-ray images of a target element arranged between the x-ray source and the x-ray detector. Since the x-rays generated by the x-ray source are divergent, the target element is shown in the x-ray images in a magnified way. Moreover, since the magnification depends on the location of the target element between the x-ray source and the x-ray detector and since this location is generally not known, it is difficult to estimate real physical dimensions of the target element based on the generated x-ray images. For instance, in stent placement procedures it is difficult to select a stent having appropriate dimensions, because it is difficult to estimate the real physical dimensions of a vessel, in which the stent should be placed.

SUMMARY OF THE INVENTION

It is an object of the present invention to provide a spatial dimension determination device, a spatial dimension determination method and a spatial dimension determination computer program for determining a spatial dimension of a target element within an object, which allows accurately providing a real physical dimension of the target element. It is a further object of the present invention to provide an interventional system comprising an introduction element like a catheter for being introduced into an object, which uses the spatial dimension determination device, and to provide a corresponding interventional method and a corresponding interventional computer program.

In a first aspect of the present invention a spatial dimension determination device for determining a spatial dimension of a target element within an object is presented, wherein the spatial dimension determination device comprises:

- a movement parameters providing unit for providing movement parameters of a moving unit, wherein the movement parameters describe a movement of an introduction element within the object by defining a sequence of positions of the introduction element within the object,
- an images providing unit for providing several images, which correspond to different times and which show the introduction element at different positions during the movement,
- a dimensional relation determination unit for determining a dimensional relation between an image dimension, which is a dimension in an image generated by the imaging unit, and a real dimension based on the generated several images and the movement parameters, and
- a real dimension determination unit, wherein the images providing unit is adapted to provide an image showing the target element within the object and wherein the real dimension determination unit is adapted to determine a real dimension of the target element within the object based on an image dimension of the target element in the image and based on the determined dimensional relation.

Since the several generated images show the position of the introduction element at different times during the movement of the introduction element in accordance with the movement parameters, a first dimension in an image space defined by the several images can be provided, wherein this first dimension can be compared with a second dimension, which is defined by the real physical positions of the introduction element during the movement as defined by the movement parameters, in order to determine the dimensional relation between an image dimension and a real physical dimension. For instance, a ratio between the first and second dimensions can be determined as the dimensional relation. After the dimensional relation has been determined, this dimensional relation can be used for determining an unknown real physical dimension of a target element within the object like a vessel of a person based on an image of this target element.

The introduction element is preferentially a catheter or a needle. It may be adapted to introduce elements into the object. For instance, the object can be a living being and the introduction element can be adapted to introduce stents into vessels of the living being.

The moving parameters preferentially define a translational movement within the object such that in this case the moving parameters may also be regarded as defining translational information.

The movement parameters providing unit can be a storing unit, in which the movement parameters are stored and from which the movement parameters can be retrieved for providing the same. The movement parameters providing unit can also be a receiving unit for receiving the movement parameters from the moving unit, wherein the movement parameters providing unit can be adapted to provide the received movement parameters.

The moving unit is preferentially a robotic unit for robotically moving the introduction element within the object in accordance with the movement parameters. Thus, the movement parameters are preferentially parameters of a robotic unit for robotically moving the introduction element within the object.

The images providing unit can also be a storing unit, in which the images are stored and from which the images can be retrieved for providing the same. Moreover, also the images providing unit can be a receiving unit for receiving the images from an imaging unit, wherein the images providing unit can be adapted to provide the received images.

In a preferred embodiment, the imaging unit is an x-ray imaging unit. For instance, the imaging unit can be an x-ray C-arm system. The images providing unit is therefore preferentially adapted to provide x-ray images of an x-ray imaging unit.

It is preferred that the movement parameters define a sequence of real positions of the introduction element covering a real dimension, and that the dimensional relation determination unit is adapted to a) detect the positions of the introduction element in the several images for determining a sequence of image positions covering an image dimension and b) determine the dimensional relation based on the image dimension covered by the sequence of image positions and based on the real dimension covered by the sequence of real positions defined by the movement parameters. This allows determining the dimensional relation accurately in a relatively simple way.

The real dimension determination unit is adapted to determine a real dimension of the target element within the object based on an image dimension of the target element in the image and based on the determined dimensional relation. Thus, for instance, if the dimensional relation has been determined as being a ratio X between a real length and an image length in the image, an actual image length of the target element can be multiplied with this ratio X for determining the real physical length of the target element.

In a further aspect of the present invention an interventional system comprising an introduction element like a catheter for being introduced into an object is presented, wherein the interventional system comprises:
  an introduction element for being introduced into the object,
  a moving unit for moving the introduction element within the object,
  an imaging unit for generating several images, which correspond to different times and which show the introduction element at different positions during the movement, and
  a spatial dimension determination device.

The images providing unit of the spatial dimension determination device is preferentially adapted to receive the several images and to provide the received images and the movement parameters providing unit of the spatial dimension determination device is preferentially adapted to receive movement parameters defining the movement of the introduction element from the moving unit and to provide the received movement parameters.

In a further aspect of the present invention a spatial dimension determination method for determining a spatial dimension of a target element within an object is presented, wherein the spatial dimension determination method comprises:
  providing movement parameters of a moving unit by a movement parameters providing unit, wherein the movement parameters describe a movement of an introduction element within the object by defining a sequence of positions of the introduction element within the object,
  providing several images, which correspond to different times and which show the introduction element at different positions during the movement, by an images providing unit,
  determining a dimensional relation between an image dimension, which is a dimension in an image generated by the imaging unit, and a real dimension based on the generated several images and the movement parameters, by a dimensional relation determination unit,
  providing an image showing the target element within the object by the images providing unit, and
  determining a real dimension of the target element within the object based on an image dimension of the target element in the image and based on the determined dimensional relation by a real dimension determination unit.

In a further aspect of the present invention an interventional method is presented, wherein the interventional method comprises:
  moving an introduction element within the object by a moving unit,
  generating several images, which correspond to different times and which show the introduction element at different positions during the movement, by an imaging unit, and
  determining a dimension of a target element within an object, according to an embodiment, wherein preferentially the several images are received and provided by the images providing unit and wherein preferentially movement parameters defining the movement of the introduction element are received from the moving unit and provided by the movement parameters providing unit.

In a further aspect of the present invention a spatial dimension determination computer program for determining a spatial dimension of a target element within an object is presented, wherein the spatial dimension determination computer program comprises program code means for causing a spatial dimension determination device to carry out steps of the spatial dimension determination method, according to an embodiment, when the spatial dimension determination computer program is run on a computer controlling the spatial dimension determination device.

In a further aspect of the present invention an interventional computer program is presented, wherein the interventional computer program comprises program code means for causing an interventional system to carry out steps of the interventional method, according to an embodiment, when the interventional computer program is run on a computer controlling the interventional system.

It shall be understood that the spatial dimension determination device, the interventional system, the spatial dimension determination method, the interventional method, the spatial dimension determination computer program, and the interventional computer program have similar and/or identical preferred embodiments, in particular, as defined in the claims.

It shall be understood that a preferred embodiment of the invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
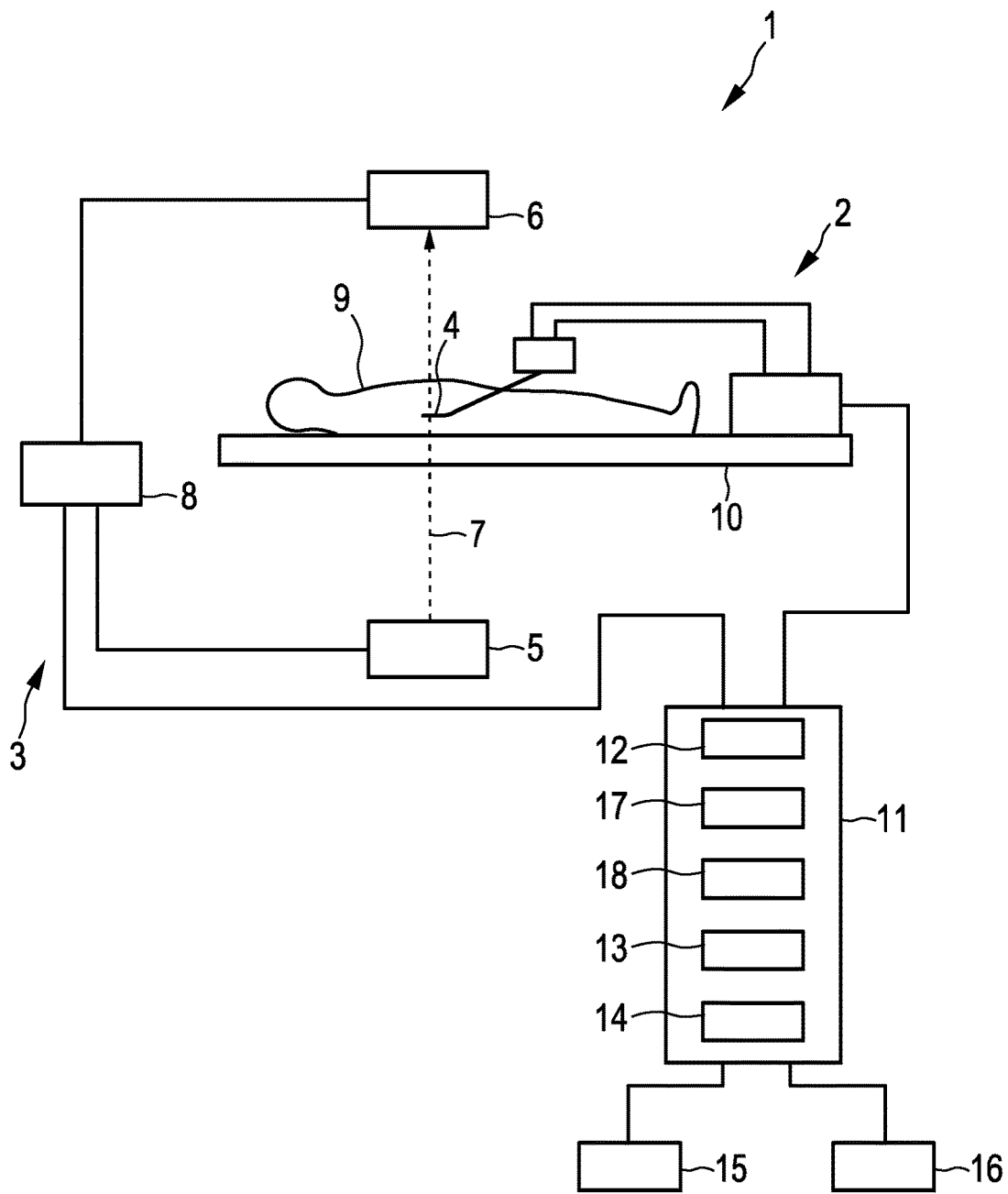
FIG. 1 shows schematically and exemplarily an embodiment of an interventional system.

FIG. 1 shows schematically and exemplarily an embodiment of an interventional system comprising an introduction element like a catheter for being introduced into an object. In this embodiment the interventional system is a catheter system 1 for introducing a catheter 4 into a person 9 lying on a support means like a patient table 10.

The catheter system 1 comprises a moving unit 2 for moving the catheter 4 within the person 9. In this embodiment the moving unit 2 is a robotic unit for robotically moving the catheter 4 within the person 9. The robotic unit 2 is controlled by a robot control unit 12 in accordance with user inputs input by a user like a physician via an input unit 15. The input unit 15 may comprise a joystick, a keyboard, a mouse, a touchpad or another means for allowing the user to control the movement of the robotic unit 2.

The movement performed by the robotic unit 2 can be described by movement parameters, which may define a sequence of positions of the catheter 4, particularly of the tip of the catheter 4, within the person 9, and by corresponding time stamps such that for each position the respective time is known. The movement parameters are transferred to a movement parameters providing unit 17, which receives the movement parameters and which can provide the received movement parameters to a dimensional relation determination unit 13.

The catheter system 1 further comprises an imaging unit 3. The imaging unit 3 is adapted to generate several images, which correspond to different times and which show the catheter 4 at different positions during the movement. In this embodiment the imaging unit 3 is an x-ray C-arm system comprising an x-ray source 5 emitting x-rays 7 for traversing the person 9 with the catheter 4. The x-ray C-arm system 3 further comprises an x-ray detector 6 for detecting the radiation 7 after having traversed the person 9 with the catheter 4. The x-ray C-arm system 3 also comprises an imaging control unit 8 for controlling the x-ray detector 6 and the x-ray source 5 and for generating x-ray projection images based on the radiation detected by the x-ray detector 6, wherein the generated images show the catheter 4, in particular, the tip of the catheter 4, within the person 9 at different positions during the movement, i.e. several images are generated, which correspond to different times during the movement of the tip of the catheter 4 within the person 9. The generated images are transferred to an images providing unit 18, which receives the generated images and which provides the received images to the dimensional relation determination unit 13. The images can also be provided to a display 16 for showing these images on the display 16.

The dimensional relation determination unit 13 is adapted to determine a dimensional relation between an image dimension, which is a dimension in an image generated by the imaging unit 3, and a real dimension based on the generated several images, which show the catheter 4, in particular the tip of the catheter 4, at different positions during the movement, and based on the movement parameters. The movement parameters define a sequence of real positions of the catheter 4, in particular of the tip of the catheter 4, covering a real dimension, for instance, covering a certain length, wherein the dimensional relation determination unit 13 is preferentially adapted to a) detect the positions of the catheter 4 in the several image for determining a sequence of image positions covering an image dimension, for instance, covering a certain length in the images, and b) determine the dimensional relation based on the image dimension, in particular, the length in the generated images, covered by the sequence of image positions and based on the real dimension, for instance, the real physical length, covered by the sequence of real physical positions defined by the movement parameters. For example, the dimensional relation can be determined as being the ratio between the real dimension covered by the sequence of real positions defined by the movement parameters and the image dimension covered by the sequence of image positions. If, for instance, the real dimension is a length Y and the image dimension is a length Z, the dimensional relation can be the ratio X=Y/Z.

After the dimensional relation, in particular, the ratio X, has been determined, this spatial relation can be used for determining a dimension of a target element shown in an image generated by the x-ray C-arm system 3. In this embodiment the target element is a vessel within the person 9, in which a stent should be placed. In order to select a stent having appropriate dimensions, the dimensions of the vessel, in which the stent should be placed, are determined. For determining this size the catheter system 1 further comprises a real dimension determination unit 14 for determining a real dimension of the target element, in particular of the vessel or of a vessel segment, within the person 9 based on an image dimension of the target element in an actual image generated by the x-ray C-arm system 3 and based on the determined dimensional relation. For instance, if in the actual image a vessel or a vessel section has a certain length, this length can be multiplied by the ratio X for determining the real physical length of the vessel or vessel section. Based on this length and possible further dimensions obtained from the image a stent having appropriate dimensions can be selected and introduced into the vessel by using the catheter 4.

Figure 2:
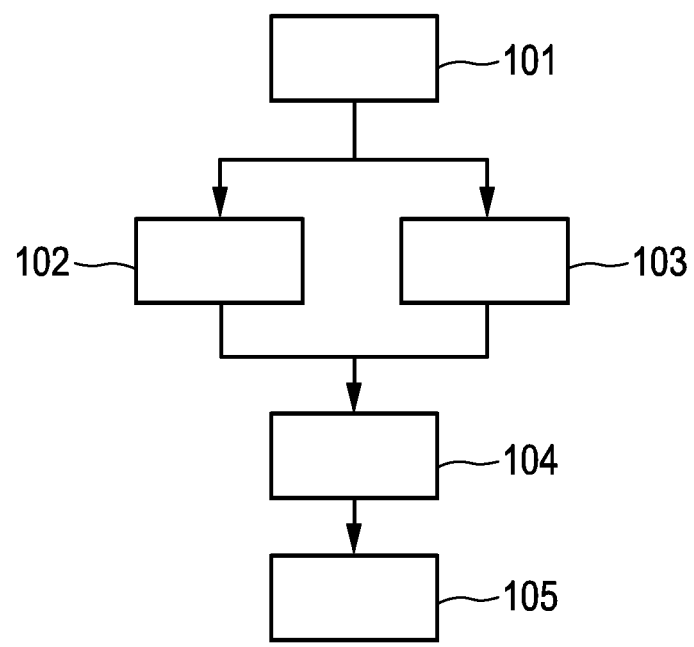
FIG. 2 shows a flowchart exemplarily illustrating an embodiment of an interventional method.

In the following an embodiment of a catheter method for introducing a catheter into a person by using the catheter system 1 will exemplarily be described with reference to a flowchart shown in FIG. 2.

In step 101 a desired movement of the tip of the catheter 4 within the person 9 is input by a user via the input unit 15. In step 102 the tip of the catheter is moved within the person by using the robotic unit 2 in accordance with the input provided by the user in step 101, while in parallel in step 103 several images are generated by the x-ray C-arm system 3, which correspond to different times and which show the tip of the catheter 4 at different positions during the movement of the catheter 4. The generated images are transferred to the images providing unit 18, which receives these images and provides them to the dimensional relation determination unit 13. Movement parameters describing the movement of the tip of the catheter 4 are transferred to the movement parameters providing unit 17, which receives these movement parameters and also provides them to the dimensional relation determination unit 13. The generated images and the movement parameters can be transferred to the images providing unit 18 and the movement parameters providing unit 17, respectively, by using wired or wireless data connections.

In step 104 a dimensional relation between an image dimension, which is a dimension in an image generated by the x-ray C-arm system 3, and a real dimension is determined based on the several images generated in step 103 and based on the movement parameters. In particular, a ratio X between a real physical length, along which the tip of the catheter 4 is moved as described by the movement parameters, and a length covering the different positions of the tip of the catheter 4 in the several images is determined. In step 105 the dimensional relation determined in step 104 is used for determining a real physical dimension of a target element shown in the images generated in step 103 or shown in another image generated by the x-ray C-arm system 3 based on a dimension of the target element in the respective generated image. For instance, a length of the target element in the respective generated image may be multiplied by the dimensional relation for determining a real physical length of the target element.

The provisions of the movement parameters and of the several images, which correspond to different times and which show the introduction element at different positions during the movement, and steps 104 and 105 can be regarded as being steps of a spatial dimension determination method for determining a spatial dimension of a target element within an object. Correspondingly, the movement parameters providing unit 17, the images providing unit 18, the dimensional relation determination unit 13 and the real dimension determination unit 14, which are comprised in a processing unit 11, can be regarded as forming a spatial dimension determination device.

The catheter system and the catheter method are preferentially adapted to perform a minimally invasive catheter procedure. It is further preferred that the catheter system and the catheter method are adapted to perform a minimally invasive catheter procedure for placing stents, in order to open constricted vessels in, for instance, a heart of a living being.

The catheter system is preferentially adapted to allow a user to accurately assess the size of a lesion, i.e. of a defected vessel, in order to allow the user to select the correct size of the stent to be placed. In particular, for accurately assessing the size of a vessel the robotic system, i.e. the robotic unit together with the robot control unit, is integrated with the x-ray equipment, i.e. with the imaging unit.

The determination of the dimensional relation can be regarded as a calibration step for calibrating the size of the features on the display 16 by using the information for controlling the robotic unit 2, i.e. by using the movement parameters. Without using the movement parameters, i.e. without using the known movement of the catheter, foreshortening can lead to an inaccurate determination of a real physical size of an element based on an image of this element. For instance, a magnification of the element in an x-ray image depends on the location between the x-ray source and the x-ray detector. If it is not precisely known, where the lesion is located along a virtual line connecting the x-ray source and the x-ray detector, the exact magnification is not known and the real physical size of the lesion can only inaccurately be determined based on the x-ray image.

Although in the embodiment described above with reference to FIG. 1 the imaging unit 3 and the processing unit 11 with the components of the spatial dimension determination device are separate units, in another embodiment the spatial dimension determination device can also be a part of the imaging unit 3, or can be regarded as being a part of the imaging unit 3, such that the moving parameters are transferred from the robotic unit 2 to the imaging unit 3. Thus, moving parameters describing a controlled movement of the catheter performed by the robotic unit 2 can be sent to the imaging unit 3 and combined with a tracking of a movement of the catheter as observed in the images generated by the imaging unit 3, in order to directly calibrate the catheter system, i.e. in order to determine the dimensional relation.

In the above described embodiments movement parameters defining a movement, i.e. a sequence of positions, of the catheter are used for calibrating the catheter system. These movement parameters, which define translational information, can be transferred from the robotic unit 2 to the movement parameters providing unit 17 via a wired or wireless data connection. Besides the movement parameters, also further information may be transferred from the robotic unit 2 to the movement parameters providing unit 17 or to another component of the processing unit 11 like the kind of catheter moved by the robotic unit 2. The kind of catheter can be indicative of the actual phase of the interventional procedure performed by the interventional system. The transferred movement parameters can include information about the shape and therewith the orientation of the catheter, i.e. the movement parameters can include information about the direction in which the catheter is pointing. This direction is the moving direction, in which the catheter is actually moved.

Since there may be some latency in the complete link chains, the catheter system is preferentially adapted to synchronize the image information obtained from the imaging unit 3 and the movement information, i.e. the real physical positions of the catheter at the different times, received from the robotic unit 2. This synchronization is important, in order to allow the dimensional relation determination unit to know which image corresponds to which real physical position of the catheter, in particular which real physical position of the tip of the catheter. Preferentially, the dimensional relation determination unit 13 uses times assigned to the sequence of real physical positions of the tip of the catheter 4 as provided by the robotic unit 2, and times, at which the generated images showing the tip of the catheter 4 during the movement have been acquired, for synchronizing the real physical positions of the tip of the catheter 4 as provided by the robotic unit 2 with the acquisition times of the generated images.

In order to determine the dimensional relation between an image dimension and a real physical dimension, the dimensional relation determination unit 13 is preferentially adapted to process the generated images such that the position of the catheter in the images is extracted. For this purpose known segmentation algorithms, which may be threshold based and/or which may be based on morphological information, or other extraction algorithms may be used. The dimensional relation determination unit 13 preferentially determines a length of a movement of the catheter, which may be flexible and bendable, along a path of motion based on the positions of the catheter extracted from the generated images. Based on this determined movement in the image, which may be quantified by the number of pixels along the path of motion, and the corresponding absolute movement as defined by the movement parameters received from the robotic unit the dimensional relation determination unit 13 can calibrate the catheter system. For example, if the movement parameters received from the robotic unit 2 indicate that the catheter 4 has been moved by 1 mm and if a shift of the tip of the catheter 4 as extracted from the images is observed to be N pixels, the size of the pixels is 1/N mm at the location of the tip of the catheter 4 such that the dimensional relation determination unit 13 can determine a corresponding dimensional relation. This calibration is done at the location of the tip of the catheter 4, which is preferentially close to the target element, which may be a lesion like a defect vessel. This results in a relatively high accuracy of the determination of the dimensions of the target element. Moreover, it is not required to estimate the exact distance of the target element to the x-ray source 5 and the x-ray detector 6, which determines the magnification.

The catheter system 1 can be adapted to continuously update the calibration, i.e. continuously determine the dimensional relation, such that the calibration is always optimized for a region around the tip of the catheter. By using the dimensional relation a change in a position observed in several images generated by the imaging unit 3 at different times can be converted into an actual real physical size by the real dimension determination unit 14.

Preferentially, the target element is a vessel and the catheter is moved within the vessel. In this case the x-ray C-arm system 3 is preferentially arranged such that a detection plane of the x-ray detector 6 is substantially parallel to the vessel.

The real dimension determination unit 14 can be adapted to measure different sizes of a target element in an image generated by the imaging unit 3, wherein these sizes can be measured in pixel units and wherein the pixel units can be converted into real physical sizes in, for instance, mm by the calibration value, i.e. by the dimensional relation determined by the dimensional relation determination unit 13. For instance, the real dimension determination unit 14 can segment a vessel in the image and determine several sizes of the segmented vessel in different directions in pixel units, wherein these sizes in pixel units can then be converted into real physical sizes in, for example, mm.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Operations like the determination of the dimensional relation between an image dimension and a real physical dimension, the determination of a real physical dimension based on the determined dimensional relation and an image dimension obtained from an actual image of an element, et cetera performed by one or several units or devices can be performed by any other number of units or devices. For example, steps 104 and 105 can be performed by a single unit or by any other number of different units. These operations and/or the control of the interventional system in accordance with the interventional method and/or the control of the spatial dimension determination device in accordance with the spatial dimension determination method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a spatial dimension determination device for determining a spatial dimension of a target element like a vessel within an object, for instance, within a person. Movement parameters describing a movement of an introduction element moved by a moving unit like a robot and several images showing the introduction element are used for determining a dimensional relation between an image dimension and a real dimension. A further image showing the target element is provided, wherein a real dimension of the target element is determined based on an image dimension of the target element in the further image and based on the determined dimensional relation. An unknown real physical dimension of a target element within the object can therefore accurately be determined from an image of the target element by using, inter alia, the movement parameters.

The invention claimed is:

1. A spatial dimension determination device for determining a real spatial dimension of a target element within a living being, the spatial dimension determination device comprising:
   a storing unit that stores:
      movement parameters of a robot describing movements by the robot of an introduction element within the living being by defining a sequence of real positions of the introduction element moving within the living being;
      a plurality of images generated by an x-ray imaging system respectively showing the introduction element at the real positions within the living being during the movements of the introduction element, and a target image generated by the x-ray imaging system showing the target element within the living being; and
   a computer processing unit in communication with the storing unit, the computer processing unit programmed to:
      receive the movement parameters of the robot and the plurality of images from the storing unit;
      determine a real dimension of a physical length covered by the sequence of real positions of the introduction element indicated by the movement parameters, and an image dimension of an image length covered by the sequence of real positions of the introduction element indicated by the plurality of images of the introduction element;
      determine a dimensional ratio between the real dimension and the image dimension; and
      determine the real spatial dimension of the target element within the living being by multiplying a target image dimension of the target element in the target image by the determined dimensional ratio.

2. The spatial dimension determination device as defined in claim 1, wherein the introduction element is a catheter or a needle.

3. An interventional system comprising:
   the spatial dimension determination device as defined in claim 1;
   the robot for moving the introduction element within the object; and
   the x-ray imaging system for generating the plurality of images and the target image showing the target element within the object, the plurality of images capturing the introduction element at different times corresponding to the real positions of the introduction element in the sequence of real positions, respectively, during movement of the introduction element within the living being by the robot.

4. An interventional computer program, stored on a non-transitory medium executable by the computer processing unit, for causing an interventional system according to claim 3 to:
   move the introduction element within the living being by the robot;

generate the plurality of images, and determine the real spatial dimension of the target element within the living being.

5. A spatial dimension determination method for determining a real spatial dimension of a target element within a living being, the spatial dimension determination method comprising:

providing movement parameters of a robot describing a movement by the robot of an introduction element within the living being by defining a sequence of real positions of the introduction element moving within the living being;

providing a plurality of images generated by x-ray imaging system respectively showing the introduction element at the real positions of the sequence of real positions within the living being during the movement of the introduction element;

determining a real dimension of a physical length covered by the sequence of real positions of the introduction element indicated by the movement parameters;

determining an image dimension of an image length covered by the sequence of real positions of the introduction element indicated by the plurality of images;

determining a dimensional ratio between the real dimension and the image dimension;

providing a target image showing the target element within the living being; and determining the real spatial dimension of the target element by multiplying an image dimension of the target element in the target image by the determined dimensional ratio.

6. The method of claim 5, wherein the introduction element is a catheter or a needle.

7. A non-transitory computer readable medium storing a spatial dimension determination computer program containing instructions for determining a real spatial dimension of a target element within a living being, the instructions, when executed by a computer processing unit, causing the computer processing unit to perform a method comprising:

providing movement parameters of a robot describing a movement by the robot of an introduction element within the living being by defining a sequence of real positions of the introduction element moving within the living being;

providing a plurality of images generated by an x-ray imaging system respectively showing the introduction element at the real positions of the sequence of real positions during the movement of the introduction element;

determining a real dimension of a physical length covered by the sequence of real positions of the introduction element indicated by the movement parameters;

determining an image dimension of an image length covered by the sequence of real positions of the introduction element indicated by the plurality of images;

determining a dimensional ratio between the real dimension and the image dimension;

providing a target image showing the target element within the living being; and determining the real spatial dimension of the target element within the living being by multiplying an image dimension of the target element in the target image by the determined dimensional ratio.

* * * * *